(12) United States Patent
Petschke

(10) Patent No.: US 10,716,527 B2
(45) Date of Patent: Jul. 21, 2020

(54) COMBINED SINOGRAM- AND IMAGE-DOMAIN MATERIAL DECOMPOSITION FOR SPECTRAL COMPUTED TOMOGRAPHY (CT)

(71) Applicant: Toshiba Medical Systems Corporation, Otawara-shi (JP)

(72) Inventor: Adam Petschke, Vernon Hills, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 668 days.

(21) Appl. No.: 15/436,043

(22) Filed: Feb. 17, 2017

(65) Prior Publication Data

US 2018/0235562 A1 Aug. 23, 2018

(51) Int. Cl.
*A61B 6/00* (2006.01)
*G06T 11/00* (2006.01)
*A61B 6/03* (2006.01)

(52) U.S. Cl.
CPC ............ *A61B 6/5205* (2013.01); *A61B 6/032* (2013.01); *A61B 6/4241* (2013.01); *A61B 6/4275* (2013.01); *A61B 6/585* (2013.01); *G06T 11/005* (2013.01); *G06T 2211/408* (2013.01)

(58) Field of Classification Search
CPC ........ G06T 11/005; A61B 6/032; A61B 6/482
See application file for complete search history.

(56) References Cited

U.S. PATENT DOCUMENTS

| 2007/0237288 A1 | 10/2007 | Tkaczyk et al. |
| 2011/0085719 A1* | 4/2011 | Fan .................. G06T 11/008 382/131 |
| 2013/0343624 A1 | 12/2013 | Thibault et al. |

OTHER PUBLICATIONS

L.A. Lehmann et al., Generalized Image Combinations in Dual KVP Digital Radiography, Departments. of Electrical Engineering and Diagnostic Radiology, Stanford University, Stanford, CA 94305, Med. Phys. 8(5), Sep./Oct. 1981, © 1981 Am. Assoc. Phys. Med. (9 pages).

* cited by examiner

*Primary Examiner* — Dani Fox
(74) *Attorney, Agent, or Firm* — Oblon, McClelland, Maier & Neustadt, L.L.P.

(57) ABSTRACT

A method and apparatus is provided to generate material-component images from spectral computed tomography (CT) projection data, using material decomposition in both the sinogram and image domains. From material components in the sinogram domain, monoenergetic sinograms are generated, and then monoenergetic images are reconstructed from the monoenergetic sinograms. Next, the monoenergetic images are decomposed into material-component images. Material decomposition in the sinogram domain enables beam-hardening corrections, and material decomposition in the image domain enhances image quality using prior information regarding the images including (e.g., smoothness and volume constraints) and using image-domain calibrations. Additionally, the method can be improved using scatter correction and detector-response and energy-spectrum calibrations. Further, iterations of the method can be performed by feeding back the material-component images to improve the scatter correction.

20 Claims, 9 Drawing Sheets

COMBINED SINOGRAM- AND IMAGE-DOMAIN MATERIAL DECOMPOSITION FOR SPECTRAL COMPUTED TOMOGRAPHY (CT)

FIELD

This disclosure relates to reconstructing images in computed tomography (CT) using material decomposition, and, more particularly, to overcoming the respective limitations of material decomposition in the sinogram and image domains by performing material decomposition in both the sinogram and image domains, as opposed to performing material decomposition only the sinogram domain or the image domain.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Those portions farther from the axis of rotation correspond to sine waves with larger amplitudes, and the phases of the sine waves correspond to the angular positions of objects around the rotation axis. Performing an inverse Radon transform—or any other image reconstruction method—reconstructs an image from the projection data represented by the sinogram.

In spectral CT, X-rays having various energies traverse a patient, are then detected using an energy-resolving detector, and reconstructed images are generated from the projection data representing the detected X-ray intensities/attenuation. For example, the respective reconstructed images can correspond to the energy bins of the energy-resolving detectors.

Alternatively, the energy-resolved projection data can be decomposed into material components corresponding to high-Z atoms and low-Z atoms. The reconstructed images can then be generated for the material-component sinograms. Often, the two material components can be a bone component and a water component, wherein the water component includes tissues and fluids primarily composed of water (e.g. blood and soft tissue).

The spectral signature of the respective materials is used to determine corresponding material projection lengths for each ray. The projection lengths represent an amount of each material component that the ray passed through on the path from the X-ray source to the X-ray detector, wherein a predefined magnitude and spectral shape is used for the X-ray absorption coefficient. Thus, the absorption represented in the projection data or image data can be transformed into material components.

Material decomposition can be achieved using various types of CT scanner configurations capable of determining the spectral differences in the X-ray attenuation, including: using energy integrating detectors in combination with an X-ray source that can selectively generate different X-ray spectra, or using a broad bandwidth X-ray source in combination with a detector that selectively detects different X-ray energy bands. For example, the photon-counting detectors differentiate between the X-rays having different energies by resolving detected X-rays into energy bins and counting the number of X-rays in each of the bins along each detector element of the detector array.

Because different materials (i.e., materials having high-Z atoms and low-Z atoms, respectively) exhibit different spectral attenuation signatures for X-rays, spectral-CT projection data can be decomposed into material components using a material-decomposition method. Material decomposition can be performed in either the sinogram domain or the image domain. Each domain has its respective advantages and drawbacks for material decomposition.

On the one hand, sinogram domain material decomposition advantageously represents beam-hardening effects accurately, but it is poorly situated to utilize a priori information regarding the imaged object, which is expressed in the image domain. On the other hand, image-domain material decomposition can advantageously use a priori information, e.g., smoothness and volume constraints, but, disadvantageously, image-domain material decomposition can be less accurate because it does not account for various physical effects (e.g., beam hardening and X-ray scatter). Current methods of material decomposition and CT image reconstruction do not simultaneously overcome the respective drawbacks of material decomposition performed in both the sinogram and image domains.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
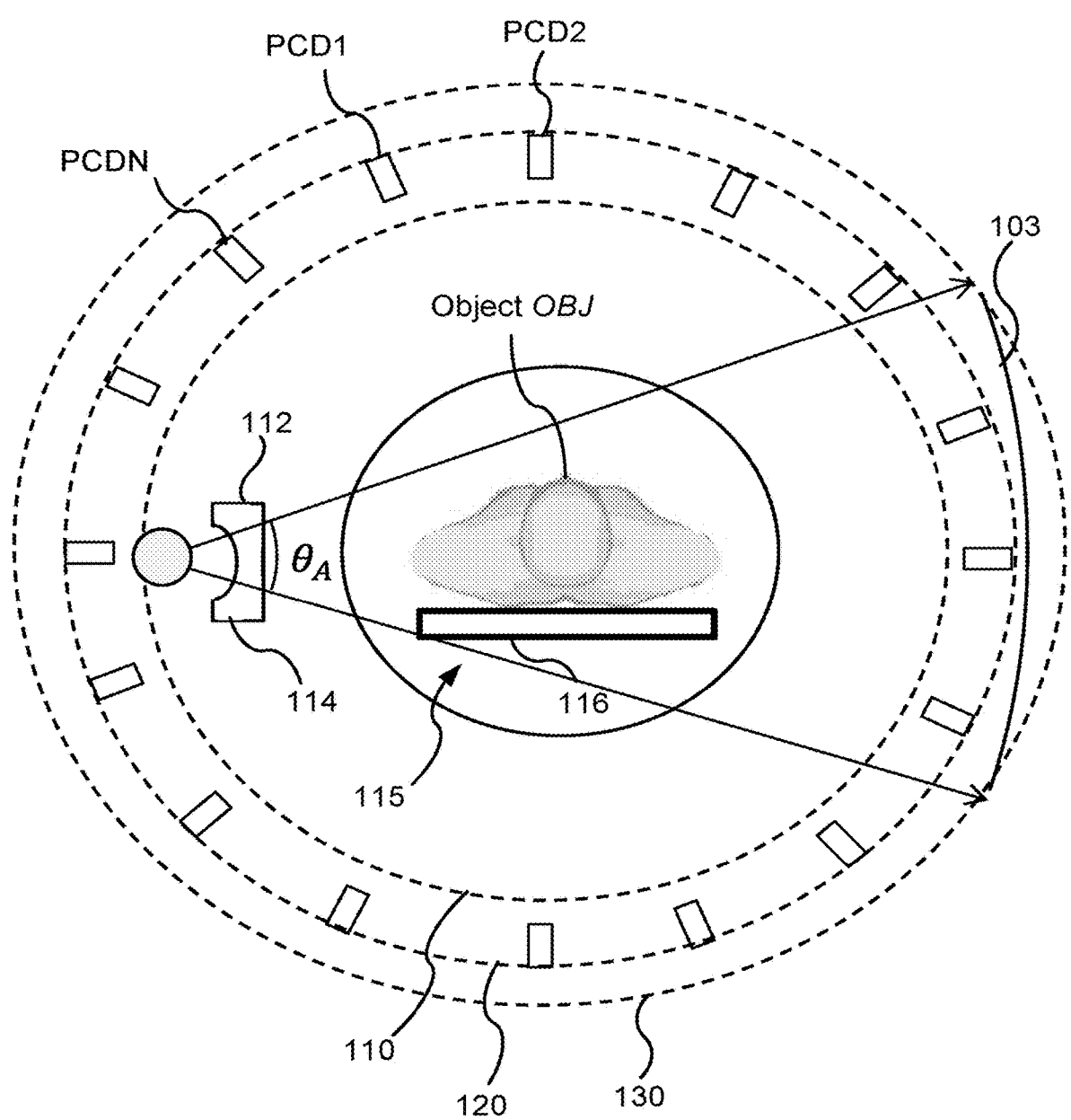
FIG. 1 shows a schematic of an implementation of an arrangement of an X-ray source and X-ray detectors for a CT scanner, according to one implementation.

In spectral computed tomography (CT), material decomposition can be performed in either the sinogram domain or the image domain. Sinogram-domain material decomposition involves transforming spectral components of the projection data into material components of the projection data. Image-domain material decomposition, on the other hand, involves solving for the material components of reconstructed images (i.e., transforming spectral components of the reconstructed images into material components). Previously, material decomposition has been performed in either the sinogram domain or the image domain, but, for a single scan of spectral CT data, material decomposition has not been simultaneously performed in both in the image domain and the sinogram domain. Indeed it would have been counterintuitive to do so because performing material decomposition in either of these domains eliminates the need to perform material decomposition in the other domain.

On the one hand, sinogram-domain material decomposition yields material-component sinograms from which material-component images are reconstructed. Because these material-component images are already represented as material components, further image-domain decomposition is unnecessary, and does not make sense.

On the other hand, image-domain material decomposition generates material-component images from spectral-component images, and these spectral-component images are reconstructed from spectral-component sinograms. Thus, sinogram-domain decomposition does not make sense in this context because material-component sinograms are not used in the image reconstruction process.

In either of the above standard cases for material decomposition, the benefits of combining sinogram- and image-domain decomposition are not readily observed because the combination would incur additional computational burdens without a clear, apparent benefit. Indeed, in view of the standard material-decomposition methods, it is not even clear how sinogram- and image-domain decomposition could be combined. However, based on the insight provided herein, the unique advantages of material decomposition in the respective sinogram and image domains can surprisingly and unexpectedly be simultaneously realized using the novel material decomposition method described herein, in which a combined material decomposition is performed in the sinogram and image domains.

Both sinogram- and image-domain material decomposition have respective advantages and disadvantages. Image-domain decomposition has the disadvantage of being less quantitatively accurate since the accuracy of the material decomposition depends on beam-hardening and scatter corrections. However, image-domain decomposition has the advantage of being capable of incorporating prior information about the imaging object by applying, e.g., smoothness and volume constraints.

In contrast to image-domain decomposition, sinogram-domain decomposition can be more quantitatively accurate because correction can accurately account for beam hardening and scatter. Further, other corrections can account for the non-linear response of the detectors, which can be significant when pileup or other non-linear effects are present. However, incorporating prior information about the object can be challenging when performing material decomposition in the sinogram domain.

The methods described herein achieve the advantages of both sinogram- and image-domain material decomposition by combining these methods as described herein. For example, beam-hardening and scatter correction can be handled exactly in the sinogram domain, and prior information, such as smoothness and volume constraints, can be handled in the image domain.

Additionally, the methods described herein are robust against inaccuracies in calibrations of the detector response and the X-ray spectrum. For standard material-decomposition methods, accurate sinogram-domain material decomposition can rely on accurate knowledge of the detector response and spectrum. The methods described herein relax requirements on how accurately the detector response and spectrum must be known. This relaxation of the calibration requirements can be achieved by correcting for small errors in the sinogram decomposition through calibrations of the image-domain decomposition.

The methods described herein combine sinogram- and image-domain material decomposition methods by using beam-hardening-free sinograms and reconstructed images as an intermediary to connect the two types of material decomposition. The description herein uses monoenergetic sinograms and reconstructed images as examples of beam-hardening-free sinograms and reconstructed images, but the methods described herein can be used with any beam-hardening-free sinograms and reconstructed images. The methods described herein achieve their advantageous results by, after material decomposition is performed in the sinogram domain, converting the material component sinograms to beam-hardening-free sinograms. Then, using the beam-hardening-free sinograms to reconstruct beam-hardening-free images before performing material decomposition in the image domain to obtain material component images.

A decomposition of the projection data into basis-specific components, which are beam hardening free, can be performed using a complete set of basis functions representing the spectral attenuation for each basis (e.g., material-component bases or attenuation-mechanism bases). For example, as explained below, the spectrally dependent attenuation of X-rays due to Compton scattering and photoelectric attenuation can provide a complete set of basis vectors/functions to represent the X-ray attenuation due to low-energy X-rays traversing through a material consisting of low-Z atoms, a scenario typical of clinical X-ray imaging applications. Also, the X-ray attenuation spectra of two material components, e.g., bone and water, can also form a complete basis when the above assumptions regarding low-Z atoms and low energy X-ray are satisfied, ensuring the avoidance of K-edges. A basis-specific decomposition into components can be transformed into another basis via a linear transformation. A beam-hardening-free representation of the sinograms and images can be generated by using the known X-ray attenuation spectra for the various basis components to determine respective beam-hardening-free representations of the sinograms and images. This process becomes clearer when considering the concrete example of using monoenergetic sinograms and images as the beam-hardening-free sinograms and images and using material components as the basis-specific components.

For example, the methods described herein can combine sinogram- and image-domain material decomposition methods by using the material-component sinograms together with energy-dependent curves of the attenuation for the respective material components to determine monoenergetic sinograms (also referred to as monoenergetic projections). Unlike spectrally resolved projections, which as a practical matter have a finite spectral width and are therefore susceptible to beam hardening, these monoenergetic sinograms respectively represent single-energy X-ray projections and are unaffected by beam hardening. Accordingly, image reconstruction can be performed on these monoenergetic sinograms to generate monoenergetic images, which are also free from the effects of beam hardening. Then a second material decomposition can be performed, this time in the image domain, to generate material-component images. This second material decomposition can then leverage the prior information of the imaged object, which contributes to the effectiveness of the image-domain reconstruction. Thus, the benefits of sinogram-domain and image-domain material decomposition can be realized by using monoenergetic representations to transition from the sinogram domain to the image domain.

In addition to applying the intermediary step of transitioning from sinogram to image domain using monoenergetic representations of the sinograms and the images, the methods described herein also advantageously incorporate various other additional features to improve the image quality of the reconstructed images. For example, the methods described herein can include scatter corrections. Additionally, the projection data (e.g., sinograms) can be preconditioned, processed, and calibrated using stored information regarding the detector response and the X-ray spectrum of the X-ray source (e.g., if the X-ray source uses a bowtie filter, then the X-ray spectrum would be measured after propagation of the X-rays through the bowtie filter).

In the methods described herein, the monoenergetic sinograms can be determined using the material-component sinograms together with known energy dependence of X-ray attenuation for the respective material components. Based on the resultant monoenergetic sinograms, monoenergetic images can be reconstructed using any known CT image reconstruction method.

Next, image-domain material decomposition can be performed on the monoenergetic images. This decomposition can incorporate prior information such as smoothness and volume constraints. Image-domain calibrations can also be used to improve the accuracy of this decomposition.

Finally, in certain implementations, the entire process described above can be repeated as an iterative loop in which the material-component images provide a model for the scatter correction, such that the scatter correction is refined with each iteration, resulting in an improved determination of the material-component images, whereby subsequent scatter corrections are improved by refinements to the material-component images and the material-component images are improved by refinements to the scatter correction. Thus, the image-domain material components can be provided to the scatter correction step to provide a more accurate model of the object that scatters the X-rays, resulting in an improved accuracy for the scatter correction. In this manner, the image reconstruction can be iterated to refine the reconstructed image by using more refined reconstructed images for the scatter correction. Accordingly, the method can be iteratively repeated by feeding back the image-domain material components into the scatter-correction model until convergence.

Referring now to the drawings, wherein like reference numerals designate identical or corresponding parts throughout the several views, FIG. 1 shows source and detector portions of a computed tomography (CT) scanner having both energy-integrating detectors arranged in a third-generation geometry and photon-counting detectors arranged in a fourth-generation geometry. Illustrated in FIG. 1 is an implementation for placing the photon-counting detectors (PCDs) in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN.

In one implementation, the X-ray source 112, the collimator/filter 114 are fixedly connected to a rotational component 110 that is rotatably connected to a gantry, and the PCDs are fixedly connected to a circular component 120 that is fixedly connected to the gantry. The gantry of the CT scanner also includes an open aperture 115 enabling the object OBJ to be placed in a projection plane of the X-rays from the X-ray source. The X-ray detector 103 is fixedly connected to a rotational component 130 that is rotatably connected to the gantry. The rotational component 120 and the rotational component 130 can rotate in unison maintaining the X-ray detector 103 diametrical opposed to the X-ray source 112 to obtain projection data of the object OBJ at a progression of projection angles. Sinograms are created by arranging the projection data with projection angles arranged along one axis and the spatial dimensions of the projection data arranged along the other axes.

In spectral CT, radiation having multiple energy components is used to make projective measurements of the object OBJ. These projective measurements are made at a series of angles enabling conventional CT image reconstruction methods similar to non-spectral CT. However, unlike non-spectral CT, spectral CT generates additional information (i.e., spectral attenuation information) enabling a decomposition of the projective measurements into material components, usually two material components. The material decomposition results in two component materials because there are two dominant interaction mechanisms causing the attenuation of the X-ray beams traversing the imaged object OBJ. These interaction mechanisms are Compton scattering and photoelectric absorption. Mapping the projection data from the spectral domain to the material domain can be performed either before or after the image reconstruction process.

The attenuation of X-rays in biological materials is dominated by two physical processes (i.e., photoelectric absorption and Compton scattering). Thus, the attenuation coefficient as a function of energy can be approximated by the decomposition $$\mu(E,x,y) = \mu_{PE}(E,x,y) + \mu_C(E,x,y),$$

wherein $\mu_{PE}(E, x, y)$ is the photoelectric attenuation and $\mu_C(E, x, y)$ is the Compton attenuation. Alternatively, this attenuation coefficient can be rearranged into a decomposition of a high-Z material (i.e., material 1) and a low-Z material (i.e., material 2) to become $$\mu(E,x,y) \approx \mu_1(E)c_1(x,y) + \mu_2(E)c_2(x,y),$$

wherein $c_1(x, y)$ and $c_2(x, y)$ are, respectively correspond to a first and second material component.

Figure 2A:
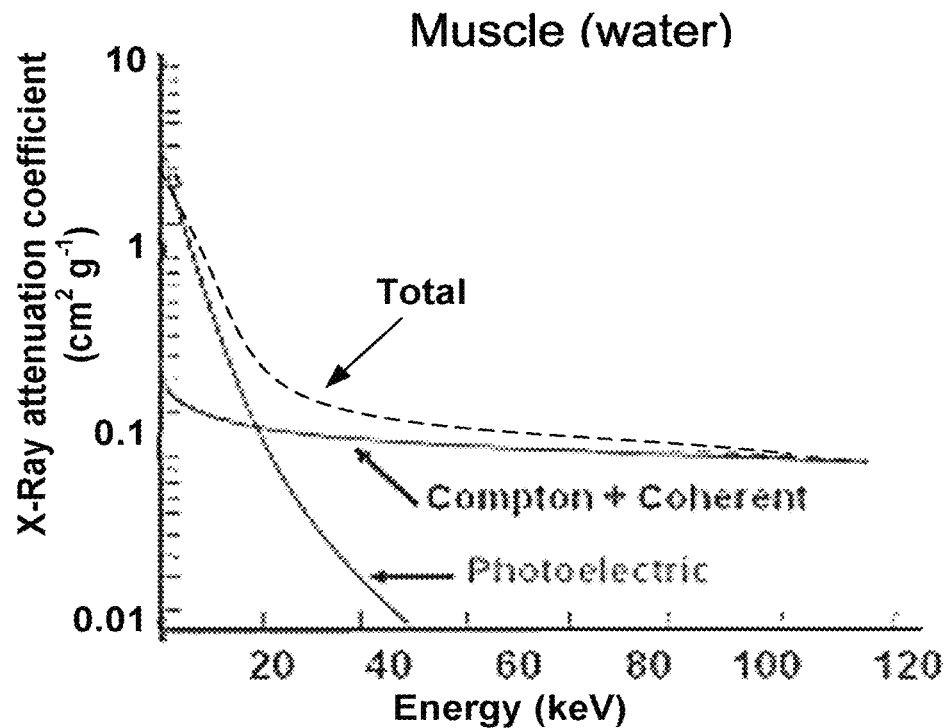
FIG. 2A shows a plot of the Compton and photoelectric contributions to X-ray attenuation in water as a function of the X-ray energy.
Figure 2B:
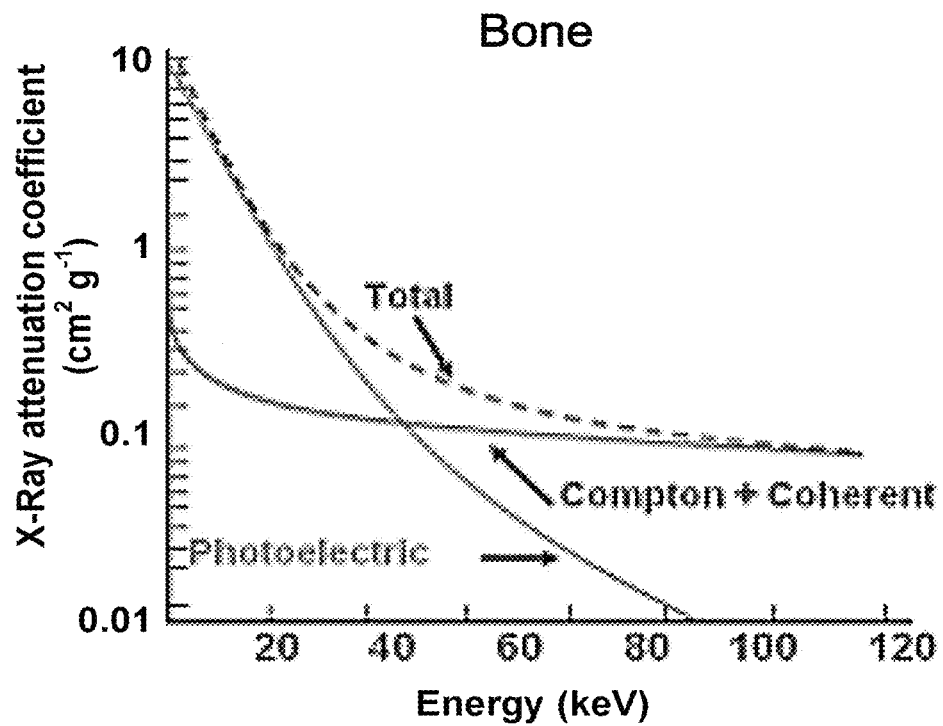
FIG. 2B shows a plot of the Compton and photoelectric contributions to X-ray attenuation in bone as a function of the X-ray energy.

FIGS. 2A and 2B show examples of absorption coefficients $\mu_1(E)$ and $\mu_2(E)$ for muscle (water) and bone respectively.

The detected spectrum is given by $$S(E_i) = S_{air}(E_i)\exp[-\mu_1(E_i)L_1 - \mu_2(E_i)L_2],$$

wherein the attenuation coefficients $\mu_1$ and $\mu_2$ are known functions of the X-ray energy, and the spectrum $S_{air}$, which correspond to the X-rays propagating through air in the absence of an absorptive object OBJ, is also known based on previous calibrations, for example. This detected spectrum can be coarse grained into X-ray energy bins (e.g., five energy bins can be used, each covering a respective energy sub-band, such that combined the energy bins span an energy spectrum from approximately 20 keV to approximately 160 keV). The count value $N_m$ of the $m^{th}$ energy bin can be given by $$N_m = \int dE\, w_m(E) S(E),$$

wherein $w_m(E)$ is a windowing function corresponding to the energy sub-band of the $m^{th}$ energy bin.

When at least two energy bins are detected for each pixel, the projection lengths $L_1(X_i)$ and $L_2(X_i)$ for each pixel of a projection image, can be estimated using the above expressions for the detected energy spectrum and the number of counts in each energy bin. The transformation from energy resolved X-ray counts to projection lengths corresponding to the first and second material components is referred to as a material decomposition. The material-component sinograms can be represented by projection lengths corresponding to the respective pixels of the two-dimensional detector array, such that the projection lengths of each material component are respectively arranged as a three-dimensional data array, in which two of the three dimensions correspond to the two axes of X-ray detector array and the third dimension corresponds to the projection angle.

Figure 3:
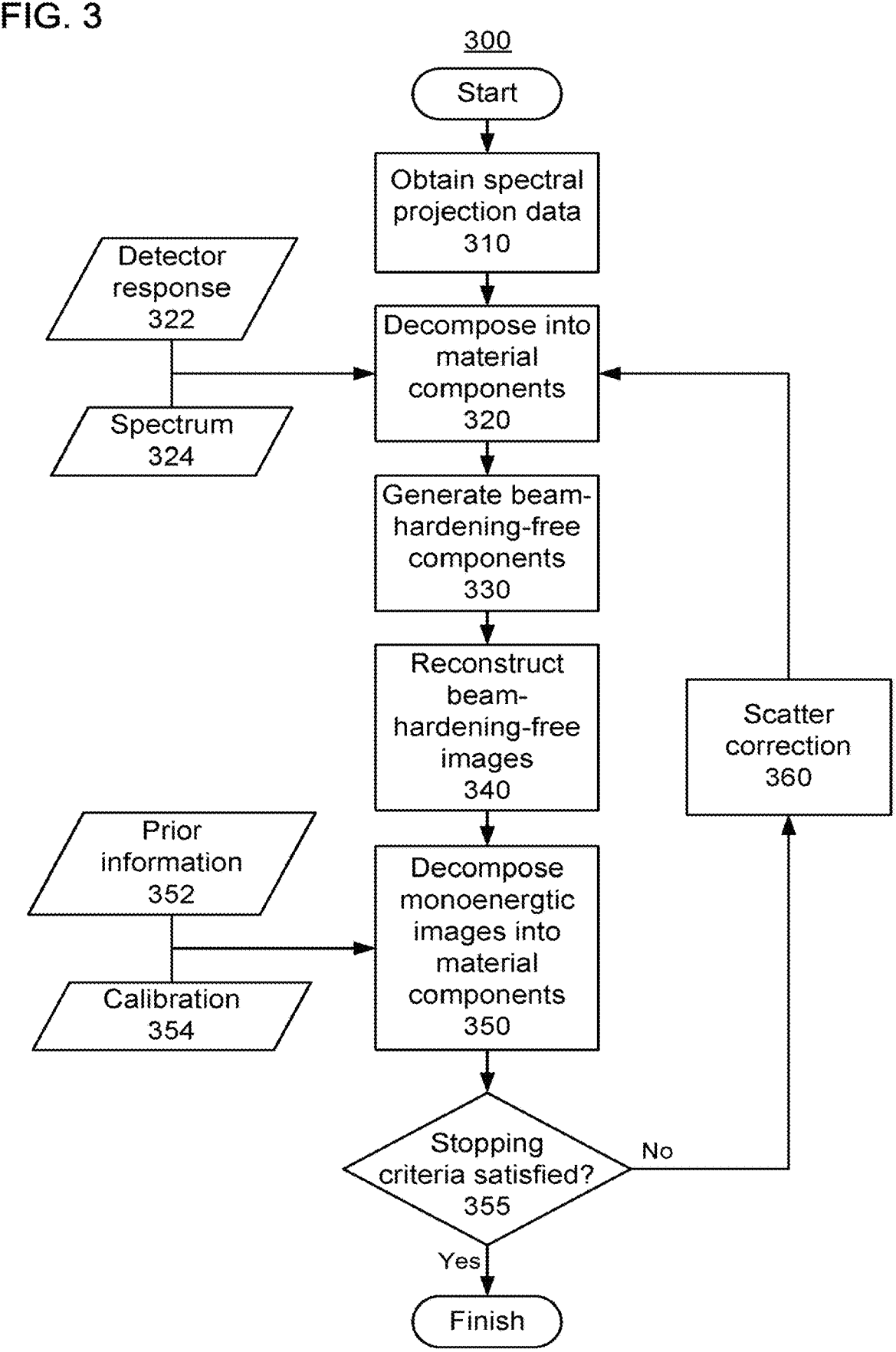
FIG. 3 shows a flow diagram of a method of combined sinogram- and image-domain material decomposition, according to one implementation.

FIG. 3 shows a flow diagram of a method 300 for performing a combined sinogram- and image-domain material decomposition.

In step 310 of method 300, spectral projection data are obtained. The spectral projection data can be obtained by performing a CT scan to measure projection images at a series of projection angles. The projection images can be resolved into energy bands, using, e.g., a direct X-ray detector which generates photoelectrons directly from X-ray radiation. Additionally, any known method of spectral CT can be used, including fast kVp switching with energy integrating detectors, spectral/energy filters, "sandwich" scintillation detectors, energy-sensitive dual-layer detectors, and dual source systems.

In step 320 of method 300, sinogram decomposition into material components is performed. For example, the material decomposition can be performed according to the methods described in U.S. patent application Ser. No. 15/017,310 ("Apparatus and Method for Material Decomposition of Spectrally Resolved Projection Data Using Singles Counts"), U.S. patent application Ser. No. 14/593,818 ("More Efficient Method and Apparatus For Detector Response Correction and Material Decomposition of Projection Data Obtained Using Photon-Counting Detectors"), U.S. patent application Ser. No. 14/603,135 ("A Cost-Function Based Method And Apparatus For Projection-Domain Basis Decomposition In Spectral Computed Tomography"), and U.S. patent application Ser. No. 14/676,594 ("A Pre-Reconstruction Calibration, Data Correction, And Material Decomposition Method And Apparatus For Photon-Counting Spectrally-Resolving X-Ray Detectors And X-Ray Imaging"), each of the aforementioned patent applications being incorporated herein by reference in its entirety. The material decomposition can include calibrations for the detector response, beam-hardening corrections, and various other calibrations and corrections. These various preparations of the projection data can variously precondition and denoise the X-ray counts to improve the image quality of reconstructed image generated therefrom and to reduce artifacts in the reconstructed images. Preconditioning the projection data can be performed using a detector response 322 and a calibrated spectrum 324 of the X-ray source. The detector response 322 and the calibrated spectrum 324 of the X-ray source can be, e.g., data that was measured previously during a calibration and stored in a computer readable memory. The material decomposition generates projection lengths for various material components, as described below.

In step 330 of method 300, the projection data is converted into monoenergetic projection images. The material decomposition transforms the projection data from spectral components to material components. Often, the projection data, when expressed in spectral components, is provided in dimensionless units of attenuation, wherein each pixel will have an attenuation value for each energy band measured by the detectors. When expressed as material components, the projection data can be expressed as projection lengths with a dimension of length, wherein, for each pixel, respective projection lengths are obtained for each of the material components (e.g., bone and water). Each material component has a predefined attenuation that is a function of the X-ray energy and has a dimension of inverse length, such that, for a given X-ray energy, the X-ray attenuation for any pixel can be determined by multiplying the respective projection lengths of the pixel with the corresponding attenuation coefficients at the given X-ray energy. This can be achieved, e.g., using the X-ray attenuation spectra for water and bone shown in FIGS. 2A and 2B. Thus, monoenergetic projection data (i.e., sinograms) can be derived from the projection lengths of the sinogram-domain material decomposition in Step 320.

In step 340 of method 300, monoenergetic images are reconstructed from the monoenergetic projection data. Any known method of image reconstruction can be used. For example, the image reconstruction process can be performed using any of a filtered back-projection method, iterative image reconstruction methods (e.g., using a total variation minimization regularization term), a Fourier-based reconstruction method, or stochastic image reconstruction methods. Reconstructed images are generated for discrete energies of the monoenergetics.

In step 350 of method 300, the monoenergetic images are decomposed into material components to generate material-component images. Any known method of material decomposition can be used. Many of the methods applied in step 320, e.g., can be straightforwardly adapted to material decomposition in the image domain, as would be understood by a person of ordinary skill in the art.

In certain implementations, prior information 352 regarding images can be used to determine the X-ray energy decomposition. For example, the prior information 352 can include which organs are being imaged and anticipated statistical properties of the reconstructed image. In another example, the prior information 352 can relate to the two material components. Consider that bone ordinarily has a higher attenuation density than water-based organs such as muscle. Accordingly, a predefined attenuation threshold can be established for volume pixels in the image domain, and volume pixels having an attenuation exceeding the attenuation threshold are presumed to be bone.

Further, the material decomposition can include a regularization term, such as a total variation (TV) minimization term or a smoothness term that imposes a constraint that the projection lengths of the image-domain material decomposition conform to a predefined characteristic. This regularization constraint can be enforced, e.g., by iteratively optimizing the projection lengths to alternatively conform to material constraint (i.e. that the attenuation spectra of the respective material components) and conform to the regularization constraint, until the projection lengths converge to s solution simultaneously satisfying both constraints.

Alternatively, a cost function representing both the material constraint and the regularization constraint can be optimized to obtain projection lengths that simultaneously satisfy both constraints.

Additionally, step 350 can use a calibration 354 to improve the material decomposition. For example, the calibration 354 can include a scan of a phantom, which has known attenuation properties, and this scan of the phantom can be used to calibrate the attenuation spectra of the material components for the material decomposition. Thus, drift or other changes in the CT scanner can be calibrated for.

The calibration 354 and the prior information 352 can be respectively previously stored calibration data and signals/flags indicating a choice regarding how the image reconstruction is performed.

In step 355 of method 300, an inquiry is performed regarding whether a stopping criteria is satisfied. In certain implementations, this step can be omitted, and method 300 can be completed after a single pass. When, however, method 300 is performed as an iterative loop, step 355 performs an inquiry whether a stopping criteria has been satisfied. These stopping criteria can include a convergence threshold, which, in certain implementations, can be performed by determining whether a predefined norm of the difference between a previous and a present reconstructed image is less than a convergence threshold. If the norm of the difference is less than the threshold, then convergence criterion is satisfied. Additionally, the stopping criteria can include a maximum-iterations criterion, in addition to the convergence criterion. If the number of iterations exceeds a predefined maximum, the maximum-iterations criterion is satisfied. In certain implementations, the stopping criteria can be satisfied if either the convergence criterion or the maximum-iterations criterion is satisfied. If the stopping criteria are satisfied method 300 is complete. Otherwise, method 300 proceeds to step 360.

In step 360 of method 300, a scatter correction can be performed to separate a primary beam of the X-rays from a scatter beam. The material decomposition in step 320 is performed on the primary beam, and the scatter beam is ignored as loss due to attenuation.

Various permutations of the steps of method 300 can be used to generate material-component reconstructed images. For example, in certain implementations, an initial image can be reconstructed in step 310 and scatter correction can be performed in step 310, such that the material decomposition in step 320 can be performed on the primary beam. For example, the initial image can be reconstructed in step 310 using a filtered back-projection or a Feldkamp-Davis-Kress reconstruction algorithm. Further, the initial image can be divided into material components using a threshold method.

In certain non-limiting implementations, the spectrally resolved intensity/attenuation for each projection pixel can be accumulated across all energy bins to create energy-integrated data, and, in certain implementations, the energy-integrated data (i.e., non-spectral data) can be corrected for beam hardening. Then a reconstructed image can be determined from the non-spectral CT projection data.

Having reconstructed an attenuation image, regions of the reconstructed image are decomposed into material components of the first and second material, wherein the spatial function describing the concentrations of material 1 and material 2 are respectively given by $$c_1(x,y) = \begin{cases} \frac{HU(x,y) + 1000}{HU_1 + 1000} & HU(x,y) < HU_1 \\ \frac{HU(x,y) - HU_1}{HU_2 - HU_1} & HU_1 \leq HU(x,y) \leq HU_2 \\ 0 & HU(x,y) > HU_2 \end{cases}, \text{ and}$$

$$c_2(x,y) = \begin{cases} 0 & HU(x,y) < HU_1 \\ \frac{HU(x,y) - HU_1}{HU_2 - HU_1} & HU_1 \leq HU(x,y) \end{cases}.$$

The constants $HU_1$ and $HU_2$ are thresholds respectively representing (i) a transition from being completely the first material to a mixed material, and (ii) a transition from being a mixed material to being completely the second material.

Having separated the reconstructed image into material components, projection lengths can be obtained by performing forward projections (e.g., Radon transforms—line integrals along the trajectories of the detected X-rays) on the spatial functions $c_1(x,y)$ and $c_2(x,y)$.

The image reconstruction problem, and also the forward projection problem, can be formulated as a matrix equation $$Af = g,$$

where g are the projection measurements of the X-rays transmitted through an object space that includes the object OBJ, A is the system matrix describing the discretized line integrals (i.e., the Radon transforms) of the X-rays through the object space, and f is the image of object OBJ (i.e., the quantity to be solved for by solving the system matrix equation). The image f is a map of the attenuation as a function of position. Thus, the projection estimates are given by $$Ac_1 = L_1 \text{ and } Ac_2 = L_2,$$

wherein $c_1$ and $c_1$ are respectively the column vector forms of the material concentrations $c_1(x,y)$ and $c_2(x,y)$. These values $L_1$ and $L_2$ can be supplied to step 320 as initial estimates of the projection lengths. Further, scatter correction can be performed using the initial reconstructed images.

Scatter correction can be performed using a model for the imaged object OBJ and a method to calculate the scatter from the imaged object OBJ. Then the primary beam P(X, Y) can be determined by subtracting the scatter beam S(X, Y) from the total measured signal T(X, Y). An X-ray beam in the presence of a scattering object can be modeled as a primary X-ray beam P(X, Y) and a scattered X-ray beam S(X, Y), wherein the projection data T(X, Y) is a composite of these two, which is given by $$T(X,Y) = P(X,Y) + S(X,Y),$$

wherein X and Y represent orthogonal spatial coordinates on the array of X-ray detectors. Different methods can be used to separate the primary beam from the scatter beam.

For example, kernel methods can be used even without a model of the object OBJ. Using a forward-scatter model, the scattered radiation S(x, y) is given by $$S(X,Y) = SF(P(X,Y)) * G_2(X,Y),$$

wherein one possible model for SF(X) is $$SF(X) = -X \log(X), \text{ and}$$

$$G_2(X,Y) = A_1 \exp[-\alpha_1(X^2+Y^2)] + A_2 \exp[-\alpha_2(X^2+Y^2)]$$

is a smoothing function that is a double Gaussian kernel with one term representing the coherent (Rayleigh) scattering and the other term representing the incoherent (Compton) scattering. The symbol "*" represents a convolution operator. The term with the coefficient $A_1$ is obtained by modeling Rayleigh scattering, and the term with the coefficient $A_2$ is obtained by modeling Compton scattering.

To correct for the scatter, a scatter simulation can be used to compute the scatter based on information of the intervening object responsible for the scatter. Given the simulated scatter, the measured projection data can be corrected by subtracting the simulated scatter.

Given the above expressions, the total beam $T(X, Y)$ can be directly calculated from a known primary beam $P(X, Y)$, but the primary beam $P(X, Y)$ cannot be calculated analytically from a known total beam $T(X, Y)$. A conventional technique, therefore, calculates an estimate of the primary beam $P_g(X, Y)$ by minimizing $$E = |T(X,Y) - T_g(X,Y)|$$

using a successive approximation method, where $T_g(X, Y)$ is a composite image calculated based on $P_g(X, Y)$, and can be represented by $$T_g(X,Y) = P_g(X,Y) + S_g(X,Y),$$

wherein $S_g(X, Y) = -P_g(X, Y) \log P_g(X, Y) * G_2(X, Y)$.

The kernel-based scatter-correction method described above does not require a model of the object OBJ, which causes the scatter. However, scatter-correction methods based on a model of the scattering object OBJ can have advantages over the kernel-based scatter-correction method. For example, using a model for the object OBJ, the scatter beam can be determined using a Monte Carlo method or a radiative transfer equation. Monte Carlo methods can be accelerated by reducing simulated photon number and fitting the simulated data. Alternatively, scatter simulation with deterministic radiative transfer equation (RTE) has the potential to provide a noise-free solution with fast simulation speed for scatter compensation. Scatter simulation using the RTE can be performed in a few seconds using GPU acceleration, but the discrete ordinate implementation using the RTE can cause a ray effect negatively impacting the precision of the simulation. These can be mitigated using spherical harmonics instead.

Figure 4:
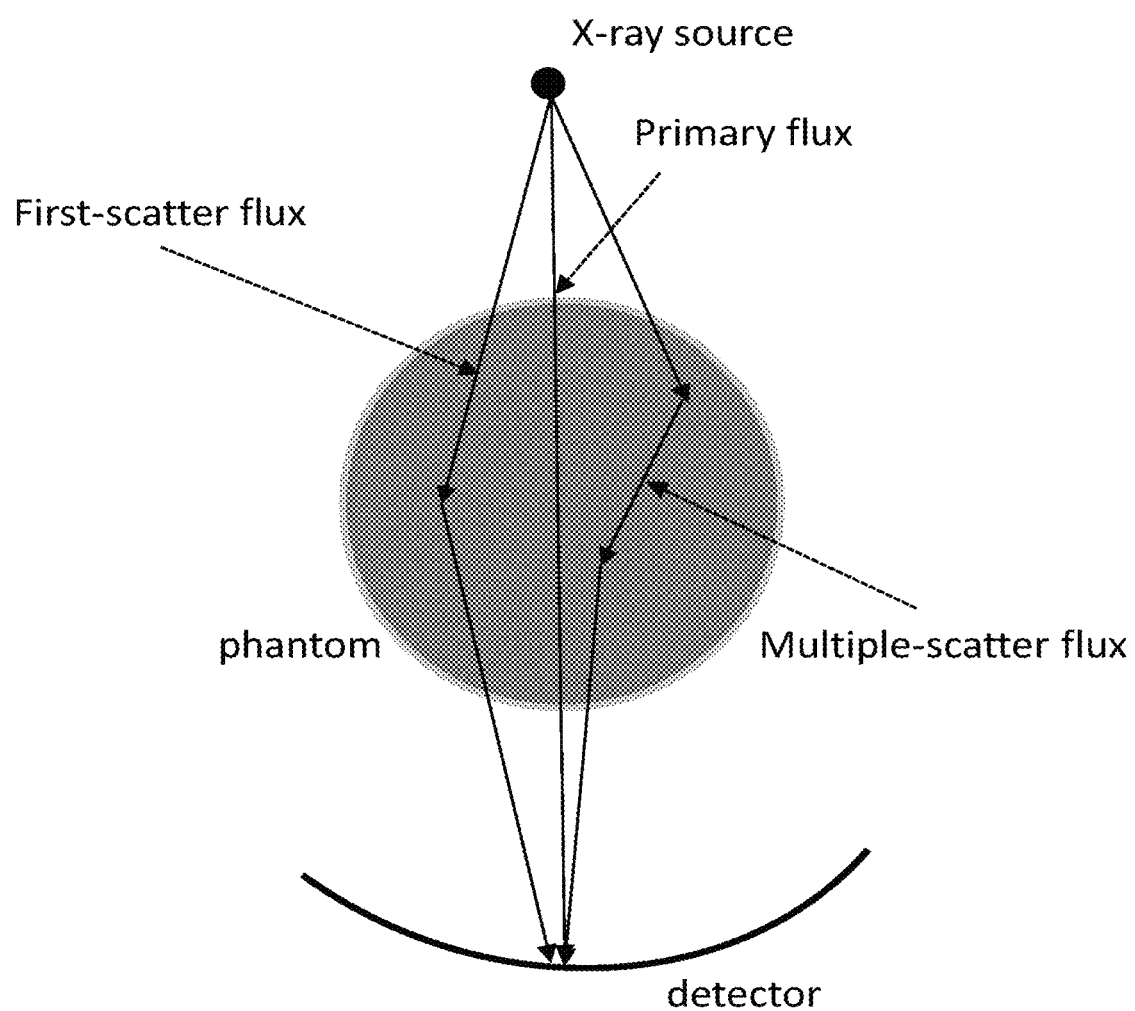
FIG. 4 shows a primary beam, first-scatter beam, and multiple-scatter beam contributions to the detected X-rays at the X-ray detector, according to one implementation.

FIG. 4 shows a diagram of the scatter process in which the primary flux is transmitted through an object, such as a phantom, and detected at a detector. The primary flux (i.e., primary beam) includes the X-rays that are not scattered. In addition to the primary flux, the detector also detects first scatter flux, which includes X-rays that have undergone one scattering event, and multiple-scatter flux, which include X-rays that have been scattered multiple times.

Scatter can be accurately simulated by including both the first-scatter flux and multi-scatter flux shown in FIG. 4 to represent an accurate physical model. This physical model can be expressed using an RTE, which is given by $$\hat{\Omega} \cdot \nabla \psi(\vec{r}, E, \hat{\Omega}) + \mu(\vec{r}, E, \hat{\Omega}) \psi(\vec{r}, E, \hat{\Omega}) = \iint d\hat{\Omega}' dE' f(\vec{r}, E, E', \hat{\Omega} \cdot \hat{\Omega}') \psi(\vec{r}, E', \hat{\Omega}'),$$

subject to the boundary condition $$\psi(\vec{r}_c, E, \hat{\Omega}) = \psi_c(\vec{r}_c, E, \hat{\Omega}), \text{ for } \hat{n} \cdot \hat{\Omega} < 0,$$

wherein $\psi(\vec{r}, E, \hat{\Omega})$ is the specific intensity of photon flux at point $\vec{r}$, E is an energy, and $\hat{\Omega}$ is unit vector in the direction of the photon flux. In the boundary condition; the intensity $\psi_c(\vec{r}_c, E, \hat{\Omega})$ depends on the X-ray source and (if a bowtie filter is used to collimator the X-ray source) on the bowtie scattering. The vector $\vec{r}_c$ indicates a point on the surface of the object, $\hat{n}$ is the normal vector to the boundary surface, and $f(\vec{r}', E, E', \hat{\Omega} \cdot \hat{\Omega}')$ is the scatter cross section, which includes both Compton and Rayleigh scattering for X-ray CT. Finally, the variable $\mu(\vec{r}'', E)$ represents the total attenuation coefficient for the X-rays at point $\vec{r}''$ and energy E.

The method described herein solves the above RTE to obtain precise scatter solution for CT scatter compensation. This is achieved by first expressing the RTE as an integral equation, which is given by $$\psi(\vec{r}, E, \hat{\Omega}) = \psi_c(\vec{r}_c, E, \hat{\Omega}) \exp\left[\int_{\vec{r}_c}^{\vec{r}} d\vec{r}'' \mu(\vec{r}'', E)\right] +$$

$$\int_{\vec{r}_c}^{\vec{r}} d\vec{r}' \iint d\hat{\Omega}' dE' f(\vec{r}', E, E', \hat{\Omega}, \hat{\Omega}')$$

$$\psi(\vec{r}', E', \hat{\Omega}') \exp\left[-\int_{\vec{r}'}^{\vec{r}} d\vec{r}'' \mu(\vec{r}'', E')\right].$$

As indicated in FIG. 4, the flux can be grouped into three components: (i) the primary flux, (ii) the first scatter flux, and (iii) the multiple scatter flux.

Next, a detector model of semiconductor-based PCDs is discussed. This model variously applies to both the cost-function method and the split-step method.

As discussed in U.S. patent application Ser. No. 13/866,965, incorporated herein by reference in its entirety, the response function of the radiation detectors can be calibrated to provide improved results. In one implementation, the detector model for the number of counts of each given radiation detector is $$N_m = T n e^{-n\tau} \iint dE dE_0 R_0(E, E_0) S(E_0) + T n^2 e^{-n\tau} \iiint dE dE_0 dE_1 R_1(E, E_0, E_1) S(E_0) S(E_1),$$

wherein each of the integrating time T, linear response function $R_0$, nonlinear response function $R_1$, and dead time $\tau$ are known for each radiation detector and energy component as a result of calibrations performed before the projective measurements on object OBJ. In the above nonlinear detector model, only the first order nonlinear term is included. Generally, higher order nonlinear terms can also be included in the detector model for the number of counts. Each integral is integrated over the spectral range for the $m^{th}$ energy bin. Thus, there is a unique count $N_m$ for each energy bin/component of each detector.

The detected spectrum is given by $$S(E_i) = S_{air}(E_i) \exp[-\mu_1(E_i) L_1 - \mu_2(E_i) L_2],$$

wherein the attenuation coefficients $\mu_1$ and $\mu_2$ are known functions of the X-ray energy, and the spectrum in the absence of an object OBJ (designated by $S_{air}$) is also known.

Similarly, the X-ray flux n for each detector is given by $$n = n_{air} \int dE_0 S(E_0) \exp[-\mu_1(E_0) L_1 - \mu_2(E_0) L_2],$$

wherein $n_{air}$ is known. In one implementation, which is discussed more completely in U.S. patent application Ser. No. 14/103,137, incorporated herein by reference in its entirety, the value of $n_{air}$ is given by $$n_{air} = A \cdot I_{ref},$$

wherein A is a calibration term unique to each detector that is determined before the projective measurements on object OBJ, and $I_{ref}$ is the reference detector signal.

The projection lengths $L_1$ and $L_2$ can be calculated by minimizing a cost function $\varphi(L_1, L_2)$ that compares the measured counts of the PCDs $N'_m = N_m^{(meas.)}$ with the calculated counts $N_m = N_m^{(model)}$ using a detector response model, such as the model discussed above. The same nomenclature is used for both the total-counts projection data and the singles-counts projection data, and in each case the correct interpretation of the nomenclature is evident to a person of ordinary skill in the art based on context. The model for the singles-counts projection data is the same as the total-counts projection data absent the higher order terms.

Several different definitions of the cost function $\varphi(L_1, L_2)$ can be used represent a difference measure between the measured counts $N'_m$ and the modeled counts $N_m$. In one implementation, the cost function is the least squares of the difference between the measured counts $N'_m$ and the modeled counts $N_m$, i.e., $$\varphi_{Pileup}(L_1, L_2) = \Sigma(N'_m - N_m)^2.$$

In one implementation, the cost function is the weighted least squares of the difference between the measured counts $N'_m$ and modeled counts $N_m$, i.e., $$\varphi_{Pileup}(L_1, L_2) = \sum \frac{(N'_m - N_m)^2}{\sigma_m^2},$$

wherein $\sigma_m$ is the standard deviation of $N'_m$.

In one implementation, the cost function is the Poisson likelihood function, i.e., $$\varphi_{Pileup}(L_1, L_2) = \Sigma[N'_m \log(N_m) - N_m].$$

The cost-function material decomposition method can be performed by using any optimization method to solve $$\arg\min_{L_1, L_2} \{\phi\}$$

in order to obtain a pair of projection lengths. If the material decomposition is constrained to a search region than a constrained optimization method can be used.

To find these local minima, any local optimization method can be used. For example, the local minima can be obtained to using any local optimization method, including: a Nelder-Mead simplex method, a gradient-descent method, a Newton's method, a conjugate gradient method, a shooting method, or other known local optimization methods.

When the cost function has more than one local minima, a robust stochastic optimization process is beneficial to find the global minimum and all of the local minima of the cost function. There are many known methods for finding global minima including: genetic algorithms, simulated annealing, exhaustive searches, interval methods, and other deterministic, stochastic, heuristic, and metaheuristic methods.

In one implementation, the method 400 shown in FIG. 4 can be used to find a minimum of a cost function. Method 400 starts when a random value is selected as the initial guess for $L^{(0)} = (L_1^{(0)}, L_2^{(0)})$. Next, at step 410 the loop variable n is incremented.

Following step 410, the method 400 proceeds to step 420, wherein a new sample point L' is randomly selected from the sample space surrounding the current set of projection lengths $L^{(n-1)} = (L_1^{(n-1)}, L_2^{(n-1)})$.

Proceeding to step 430, the method 400 inquiries as to which of value of the cost function $\varphi(L^{(n-1)})$ or $\varphi(L')$ is smaller. In steps 440 and 450 the argument corresponding to the smaller value of the cost function is assigned as the next set of projection lengths $L^{(n)} = (L_1^{(n)}, L_2^{(n)})$ for the next loop iteration.

Step 460 of method 400 evaluates whether the loop stopping criteria is satisfied. Although different stopping criteria can used, FIG. 4 shows an implementation wherein the loop stops when either a maximum number of loop iterations $n_{max}$ has been reached or the cost function falls below a predetermined threshold $\epsilon$. If the stopping criteria are satisfied, the method 400 exits the loop at 460 and reports the current projection length $L^{(n)} = (L_1^{(n)}, L_2^{(n)})$ as the final projection length. Otherwise, the loop continues by proceeding from step 460 back to step 410.

In addition to the cost-function method discussed above, a split-step method of performing the material decomposition is discussed in U.S. patent application Ser. No. 14/593,818, incorporated herein by reference in its entirety. This split-step method solves the material decomposition problem by alternating between using projection length estimates to correct the measured counts for the nonlinear response of the PCDs and then using the corrected counts to generate new projection length estimates.

Figure 5:
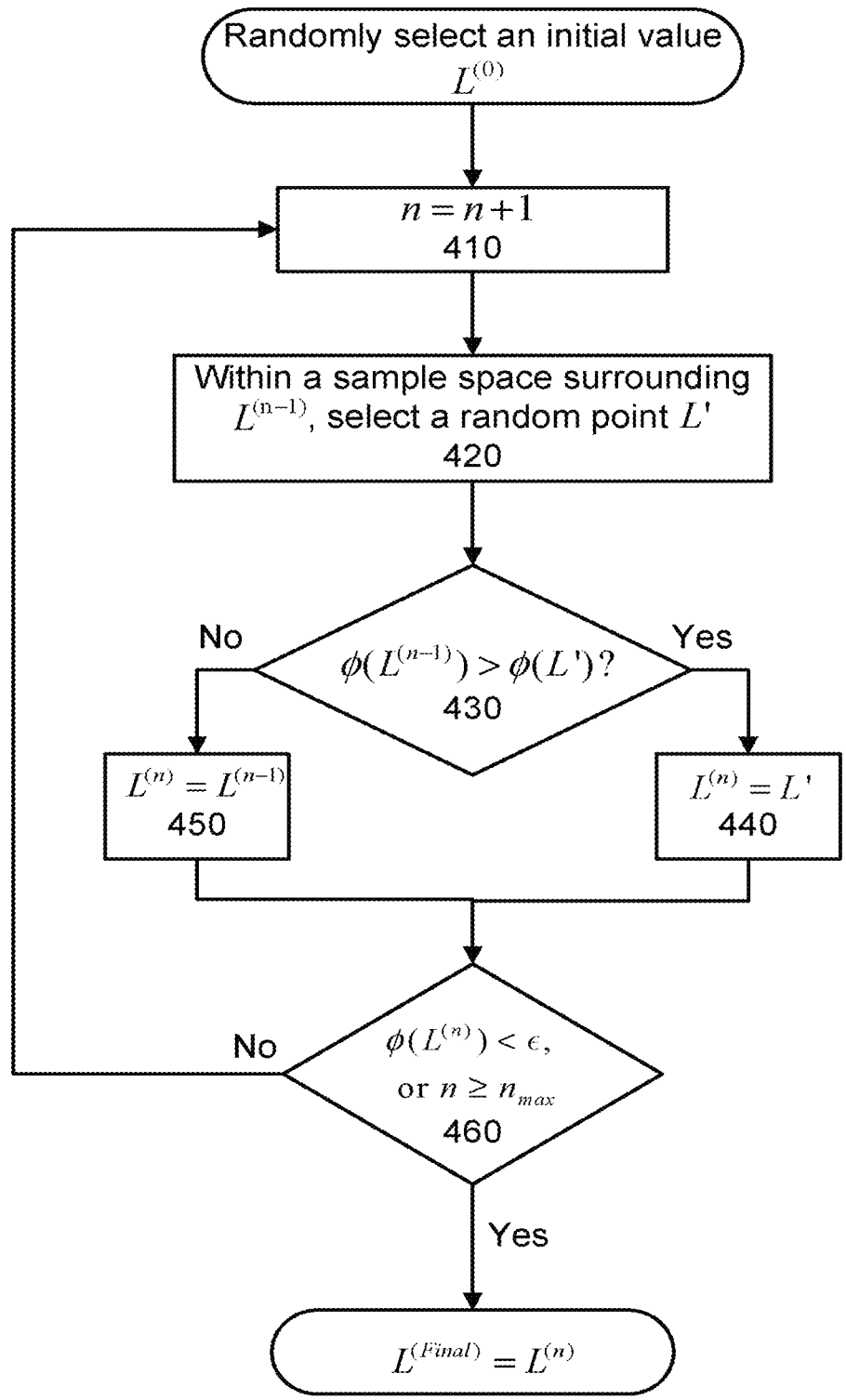
FIG. 5 shows a flow diagram of an implementation of a cost-function method to perform material decomposition.

FIG. 5 shows one implementation of the split-step method 500. In FIG. 5, a split-step method 500 for solving the material decomposition problem is exemplified for the case of total-counts projection data. This method solves for the projection lengths $L^{Final} = (L_1, L_2)$.

As shown in FIG. 5, method 500 begins when an initial estimate of the projection lengths $L_1$ and $L_2$ are input into the first step 520 of an iterative loop. After the first iteration of the large loop including steps 520 through 560, the projection lengths $L_1$ and $L_2$ are fed back from material decomposition in process 550 to the first step 520 of the large iterative loop. In contrast to subsequent loop iterations using projection lengths calculated by the material decomposition in process 550, the first iteration uses the initial estimate of the projection lengths from step 510.

Receiving the projection length estimates, the large loop begins at step 520 by calculating the X-ray flux rate $$n = n_{air} \int dE_0 S_{air}(E_0) \exp[-\mu_1(E_0)L_1 - \mu_2(E_0)L_2],$$

and the nonlinear spectrum term $S_{Nonlin.}(E)$ discussed previously. In the implementation shown in FIG. 5, the nonlinear spectrum includes only the first order pileup, which is given by $$S_{1,out}(E) = \iint dE_0 dE_1 R_1(E, E_0, E_1) S_{in}(E_0) S_{in}(E_1),$$

wherein $$S_{in}(E) = S_{air}(E) \exp[-\mu_1(E)L_1 - \mu_2(E)L_2].$$

Next at step 430 of method 400, the corrected detector spectrum is calculated to correct for pileup as given by $$S_{Corr.}(E) = S_{Raw}(E) - S_{Nonlin.}(E),$$

wherein $S_{Raw}(E)$ is the raw measured spectrum before detector response corrections. The corrected energy count is given by $$N_m^{Corr.} = T \int dE W_m(E) S_{Corr.}(E),$$

wherein T is the integration time. For the singles-counts projection data the higher order corrections associated with pileup can be omitted.

In one implementation, the corrected count of the $m^{th}$ energy bin of the PCD is given by $$N_m^{Corr.} = N_m^{Raw} - N_m^{Nonlin.}$$

wherein $N_m^{Corr.}$ is the corrected count value of the $m^{th}$ energy bin of the PCD, $N_m^{Raw}$ is the raw count value recorded from the detector, and $N_m^{Nonlin.}$ is the calculated count from the nonlinear detector response. The nonlinear count value $N_m^{Nonlin.}$ is calculated according to $$N_m^{Nonlin.} = T\int dE\, w_m(E) S_{Nonlin.}(E).$$

In some implementations, the nonlinear spectrum correction includes only the first order pileup; while in other implementations, the nonlinear spectrum correction includes higher-order pileup terms. For example, higher order terms can be omitted for singles-counts projection data.

The method 500 then proceeds to step 540. In step 540, noise balancing is performed by dividing the detector counts into high- and low-energy components in preparation for material decomposition. The noise-balancing process of apportioning the counts into high- and low-energy components is described in U.S. patent application Ser. No. 13/906,110, incorporated herein by reference in its entirety. The noise balancing in step 540 results in partitioning the counts from the energy bins into high- and low-energy components according to $$N_H = \sum_m a_m^{(H)} N_m^{Corr.}, \text{ and}$$

$$N_L = \sum_m a_m^{(L)} N_m^{Corr.},$$

wherein $\sum_m a_m^{(H)} = 1$, $\sum_m a_m^{(L)} = 1$, and the values $a_m^{(H)}$ and $a_m^{(L)}$ are determined by the noise-balancing process.

Next method 500 proceeds to process 550. In process 550 the material decomposition is performed, wherein new values for the projection lengths $L_1$ and $L_2$ are calculated.

Finally, at step 560, an inquiry is made into whether the stopping criteria have been satisfied. The stopping criteria can depend on convergence of the projection lengths $L_1$ and $L_2$, and whether the maximum number of loop iterations have been reached.

Figure 6:
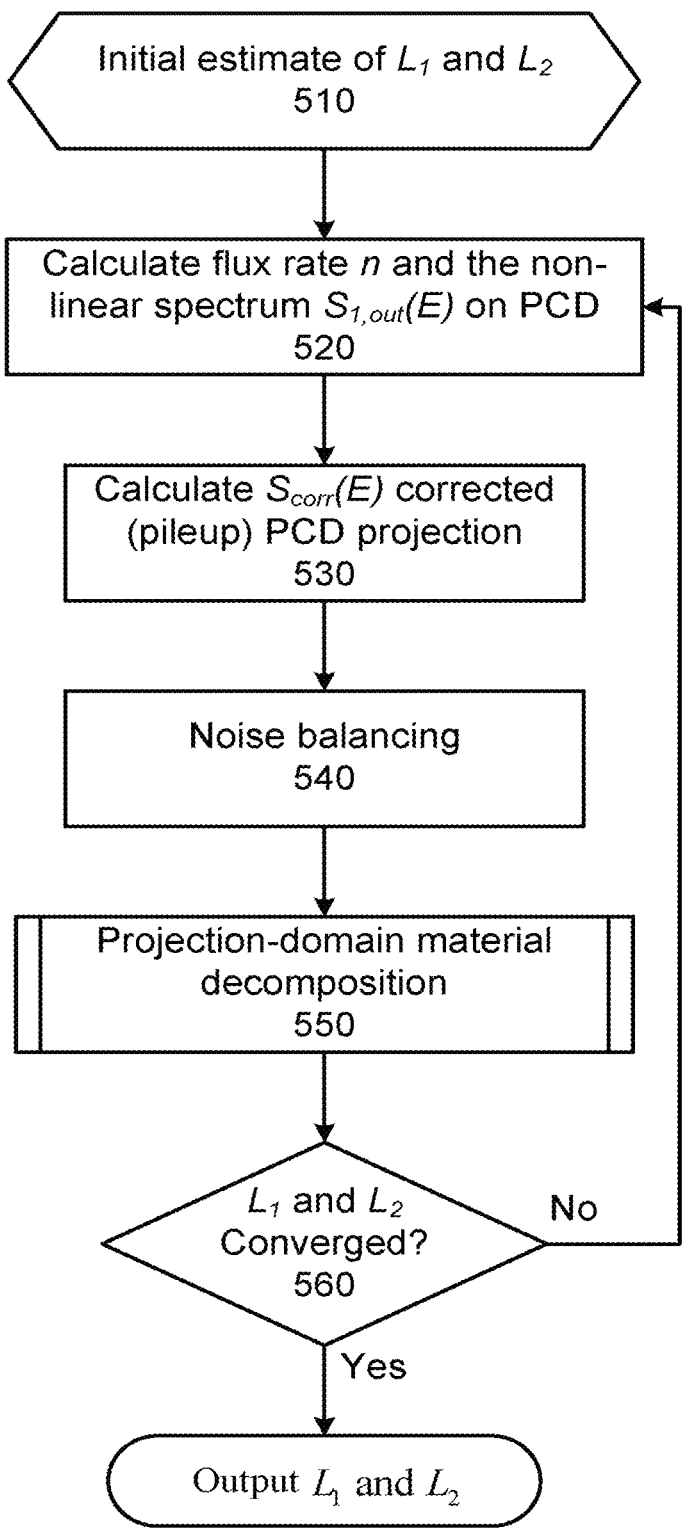
FIG. 6 shows a flow diagram of an implementation of a split-step method to perform material decomposition.
Figure 7:
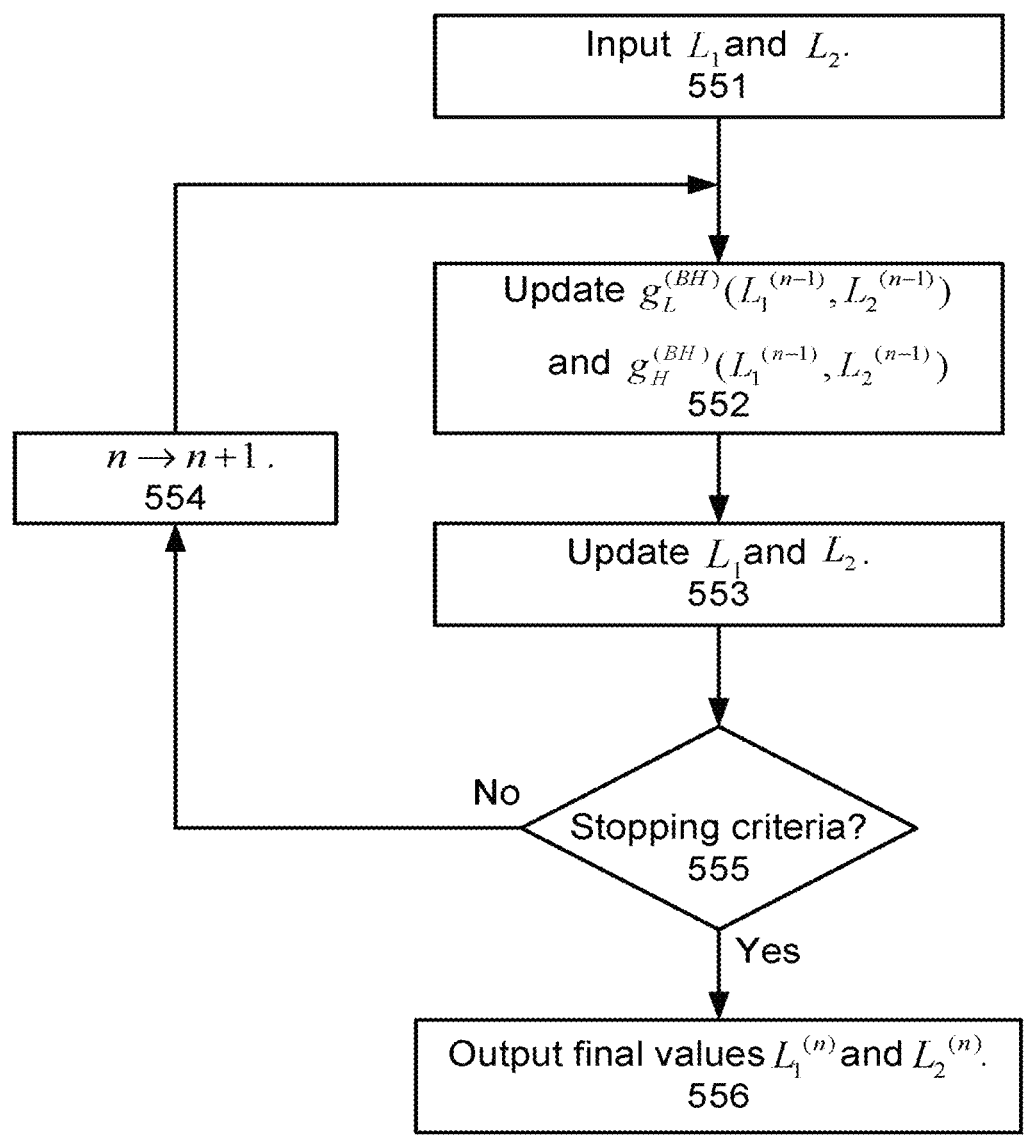
FIG. 7 shows a flow diagram of an implementation of a projection-domain material decomposition process with beam-hardening corrections.

The material decomposition process 550 can be an iterative process—as shown in FIG. 6—with its own stopping criteria. This iterative process can be referred to as the small loop, in contrast to the large loop including steps 555 through 560.

In one implementation, process 550 is performed according to the method shown in FIG. 6, as discussed in U.S. Pat. No. 8,194,961, incorporated herein by reference in its entirety. Similar to the detector counts for the high- and low-energy components, the high and low spectra can be given by $$S_H(E) = \sum_m a_m^{(H)} S_{air}(E), \text{ and}$$

$$S_L(E) = \sum_m a_m^{(L)} S_{air}(E),$$

wherein $S_H(E)$ and $S_L(E)$ are respectively the detected high- and low-energy spectra in the absence of the object OBJ (i.e., the object OBJ is air), and where $S_H(E)$ and $S_L(E)$ have been normalized such that $$\int dE\, S_H(E) = \int dE\, S_L(E) = 1.$$

By taking the natural logarithm of the detector counts, the log-projection data can be obtained as $$g_H(l) = -\ln(N_H/N_H^{air}) \text{ and}$$

$$g_L(l) = -\ln(N_L/N_L^{air}).$$

In one implementation, $L_1$ and $L_2$ are found using perturbation theory by treating the variations around the mean of the attenuation coefficients $\mu_1(E)$ and $\mu_2(E)$ as perturbations.

First, the mean attenuation for the high- and low-energy spectra are given by $$\bar{\mu}_{1,2}^{H,L} = \int S_{H,L}(E) \mu_{1,2}(E) dE,$$

and the variations around the mean are given by $$\Delta\mu_{1,2}^{H,L}(E) = \mu_{1,2}(E) - \bar{\mu}_{1,2}^{H,L}.$$

Thus, the log-projection data can be expressed as $$g_H(l) = -\ln\int S_H(E) \exp[-\bar{\mu}_1^H L_1(l) - \Delta\mu_1^H(E) L_1(l) - \bar{\mu}_2^H L_2(l) - \Delta\mu_2^H(E) L_2(l)] dE$$

$$g_L(l) = -\ln\int S_L(E) \exp[-\bar{\mu}_1^L L_1(l) - \Delta\mu_1^L(E) L_1(l) - \bar{\mu}_2^L L_2(l) - \Delta\mu_2^L(E) L_2(l)] dE.$$

Simplifying these expressions, the log-projection data can be written as $$g_H(l) = \bar{\mu}_1^H L_1(l) + \bar{\mu}_2^H L_2(l) - g_H^{(BH)}(L_1(l), L_2(l))$$

$$g_L(l) = \bar{\mu}_1^L L_1(l) + \bar{\mu}_2^L L_2(l) - g_L^{(BH)}(L_1(l), L_2(l))$$

wherein $$g_{H,L}^{(BH)}(L_1(l), L_2(l)) = \ln\int S_{H,L}(E) \exp[-L_1(l)\Delta\mu_1^{H,L}(E) - L_2(l)\Delta\mu_2^{H,L}(E)] dE$$

is the beam-hardening perturbation.

The first step 551 of process 550 initializes the iteration variable to n=0 and also initializes the values of the projection lengths $L_1$ and $L_2$. In one implementation, the initial values of the projection lengths are the same values used for the detector response correction calculation in step 555. In another implementation, the initial values of the projection lengths are the zeroth-order perturbation values calculated by solving the matrix equation $$\begin{pmatrix} g_H \\ g_L \end{pmatrix} = \begin{pmatrix} \bar{\mu}_1^H & \bar{\mu}_2^H \\ \bar{\mu}_1^L & \bar{\mu}_2^L \end{pmatrix} \begin{pmatrix} L_1 \\ L_2 \end{pmatrix}$$

to obtain $$\begin{pmatrix} L_1 \\ L_2 \end{pmatrix} = D^{-1} \begin{pmatrix} \bar{\mu}_2^L & -\bar{\mu}_2^H \\ -\bar{\mu}_1^L & \bar{\mu}_1^H \end{pmatrix} \begin{pmatrix} g_H \\ g_L \end{pmatrix}$$

wherein D is the determinant $D = \bar{\mu}_1^H \bar{\mu}_2^L - \bar{\mu}_1^L \bar{\mu}_2^H$.

The second step 552 of process 550, which is also the first step in the iterative loop, updates the beam-hardening perturbation values using the $n^{th}$ order perturbation in the equation $$g_{H,L}^{(BH)}(L_1(l), L_2(l)) = \ln\int S_{H,L}(E) \exp[-L_1(l)\Delta\mu_1^{H,L}(E) - L_2(l)\Delta\mu_2^{H,L}(E)] dE.$$

The third step 553 of process 550 is to update the values of $L_1$ and $L_2$ by solving for the $n+1^{th}$ perturbation by solving the matrix equation $$\begin{pmatrix} g_H + g_H^{(BH)}(L_1, L_2) \\ g_L + g_L^{(BH)}(L_1, L_2) \end{pmatrix} = \begin{pmatrix} \overline{\mu}_1^H & \overline{\mu}_2^H \\ \overline{\mu}_1^L & \overline{\mu}_2^L \end{pmatrix} \begin{pmatrix} L_1 \\ L_2 \end{pmatrix}$$

to obtain $$\begin{pmatrix} L_1^n \\ L_s^n \end{pmatrix} = D^{-1} \begin{pmatrix} \overline{\mu}_2^L & -\overline{\mu}_2^H \\ -\overline{\mu}_1^L & \overline{\mu}_1^H \end{pmatrix} \begin{pmatrix} g_H + g_H^{(BH)}(L_1^{n-1}, L_2^{n-1}) \\ g_L + g_L^{(BH)}(L_1^{n-1}, L_2^{n-1}) \end{pmatrix}.$$

After step 554, step 555 of process 550 inquiries whether the stopping criteria have been satisfied. In one implementation, the stopping criteria are satisfied when the values $L_1$ and $L_2$ satisfy a predetermined convergence criteria, such as whether the difference between each current and previous values of $L_1$ and $L_2$ are less than a predefined threshold. The stopping criteria can also be conditioned on whether a maximum number of iterations have been reached. If stopping criteria have not been satisfied, then the loop variable n is incremented at step 554 and the loop begins again starting from step 552. Otherwise, the final projection lengths are output at step 556 of process 550.

At various points in steps 320, 340, 350, and 360 the sinogram and image data can be variously denoised to improve the image quality of the reconstructed images, including: linear smoothing filters, anisotropic diffusion, non-local means, and nonlinear filters.

Linear smoothing filters remove noise by convolving the original image with a mask that represents a low-pass filter or smoothing operation. For example, the Gaussian mask comprises elements determined by a Gaussian function. This convolution brings the value of each pixel into closer agreement with the values of its neighbors. In general, a smoothing filter sets each pixel to the average value, or a weighted average, of itself and its nearby neighbors; the Gaussian filter is just one possible set of weights. Disadvantageously, smoothing filters tend to blur an image because pixel intensity values that are significantly higher or lower than the surrounding neighborhood are smeared or averaged across their neighboring area. Sharp boundaries become fuzzy. Generally, local linear filter methods assume that local neighbourhood are homogeneous, and local linear filter methods, therefore, tend to impose homogeneity on the image obscuring non-homogeneous features, such as lesions or organ boundaries.

Anisotropic diffusion removes noise while preserving sharp edges by evolving an image under a smoothing partial differential equation similar to the heat equation. If the diffusion coefficient were spatially constant, this smoothing would be equivalent to linear Gaussian filtering, but when the diffusion coefficient is anisotropic according to the presence of edges, the noise can be removed without blurring the edges of the image.

A median filter is an example of a nonlinear filter and, if properly designed, a nonlinear filter can also preserve edges and avoid blurring. A median filter operates, for example, by evaluating each pixel in the image, sorting the neighboring pixels according to intensity, and replacing the original value of the pixel with the median value from the ordered list of intensities. The median filter is one example of a rank-conditioned rank-selection (RCRS) filter. For example, median filters and other RCRS filters can be applied to remove salt and pepper noise from an image without introducing significant blurring artifacts.

In addition a filter using a total-variation (TV) minimization regularization term can be used where it is assumed that the areas being imaged are uniform over discrete areas with relatively sharp boundaries between the areas. A TV filter can also be used as another example of a nonlinear filter.

In non-local means filtering, rather than performing a weighted average of pixels according to their spatial proximity, pixels are determined to be a weighted average according to the similarity between patches within the images. Thus, noise is removed based on non-local averaging of all the pixels in an image—not just the neighboring pixels. In particular, the amount of weighting for a pixel is based on the degree of similarity between a small patch centered near that pixel and another small patch centered on the pixel being denoised.

Figure 8:
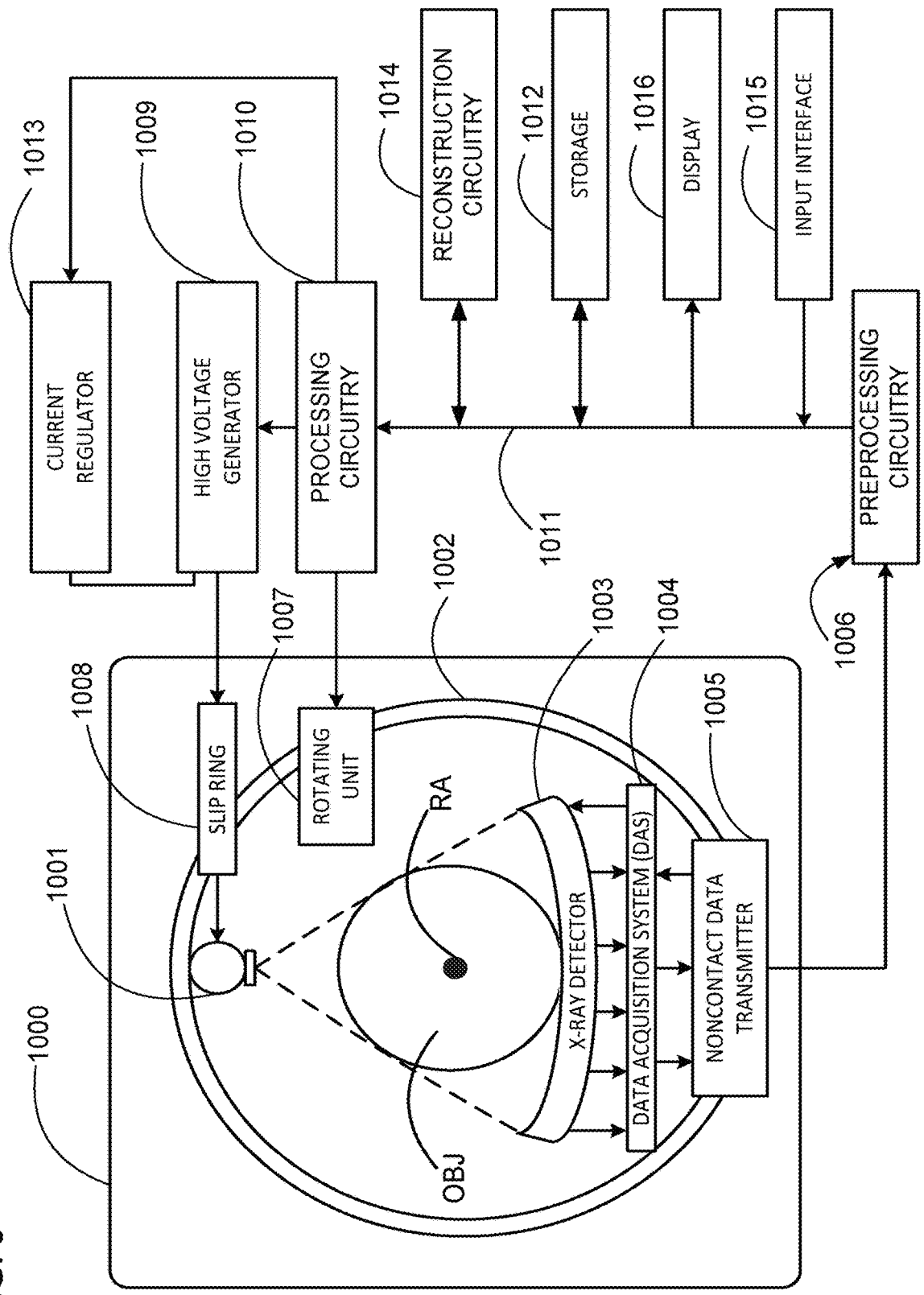
FIG. 8 shows a schematic of an implementation of a CT scanner using a third-generation geometry, according to one implementation.

FIG. 8 illustrates an implementation of the radiography gantry included in a CT apparatus or scanner. As shown in FIG. 8, a radiography gantry 1000 is illustrated from a side view and further includes an X-ray tube 1001, an annular frame 1002, and a multi-row or two-dimensional-array-type X-ray detector 1003. The X-ray tube 1001 and X-ray detector 1003 are diametrically mounted across an object OBJ on the annular frame 1002, which is rotatably supported around a rotation axis RA. A rotating unit 1007 rotates the annular frame 1002 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 1009 that generates a tube voltage applied to the X-ray tube 1001 through a slip ring 1008 so that the X-ray tube 1001 generates X-rays. The X-rays are emitted towards the object OBJ, whose cross sectional area is represented by a circle. For example, the X-ray tube 1001 having an average X-ray energy during a first scan that is less than an average X-ray energy during a second scan. Thus, two or more scans can be obtained corresponding to different X-ray energies. The X-ray detector 1003 is located at an opposite side from the X-ray tube 1001 across the object OBJ for detecting the emitted X-rays that have transmitted through the object OBJ. The X-ray detector 1003 further includes individual detector elements or units.

The CT apparatus further includes other devices for processing the detected signals from X-ray detector 1003. A data acquisition circuit or a Data Acquisition System (DAS) 1004 converts a signal output from the X-ray detector 1003 for each channel into a voltage signal, amplifies the signal, and further converts the signal into a digital signal. The X-ray detector 1003 and the DAS 1004 are configured to handle a predetermined total number of projections per rotation (TPPR).

The above-described data is sent to a preprocessing circuitry 1006, which is housed in a console outside the radiography gantry 1000 through a non-contact data transmitter 1005. The preprocessing circuitry 1006 performs certain corrections, such as sensitivity correction on the raw data. A storage 1012 stores the resultant data, which is also called projection data at a stage immediately before reconstruction processing. The storage 1012 is connected to a processing circuitry 1010 through a data/control bus 1011, together with a reconstruction device 1014, input interface 1015, and display 1016. The processing circuitry 1010 controls a current regulator 1013 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1001 and the X-ray detector 1003 are diametrically mounted on the annular frame 1002 and are rotated around the object OBJ as the annular frame 1002 is rotated about the rotation axis RA. In the fourth-generation geometry system, the detectors are fixedly placed around the patient and an X-ray tube rotates around the patient. In an alternative embodiment, the radiography gantry 1000 has multiple detectors arranged on the annular frame 1002, which is supported by a C-arm and a stand.

The storage 1012 can store the measurement value representative of the irradiance of the X-rays at the X-ray detector unit 1003. Further, the storage 1012 can store a dedicated program for executing methods 300, 400, and 500.

The reconstruction circuitry 1014 can execute various steps of methods 300, 400, and 500. Further, reconstruction circuitry 1014 can execute pre-reconstruction processing image processing such as volume rendering processing and image difference processing as needed.

The pre-reconstruction processing of the projection data performed by the preprocessing circuitry 1006 can include correcting for detector calibrations, detector nonlinearities, and polar effects, for example. Further, the pre-reconstruction processing can include various steps of methods 300, 400, and 500.

Post-reconstruction processing performed by the reconstruction circuitry 1014 can include filtering and smoothing the image, volume rendering processing, and image difference processing as needed. The image reconstruction process can implement various steps of methods 300, 400, and 500. The reconstruction circuitry 1014 can use the memory to store, e.g., projection data, reconstructed images, calibration data and parameters, and computer programs.

The reconstruction circuitry 1014 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 1012 can be non-volatile, such as ROM, EPROM, EEPROM or FLASH memory. The storage 1012 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction circuitry 1014 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1016. The display 1016 can be an LCD display, CRT display, plasma display, OLED, LED or any other display known in the art.

The storage 1012 can be a hard disk drive, CD-ROM drive, DVD drive, FLASH drive, RAM, ROM or any other electronic storage known in the art.

Figure 9:
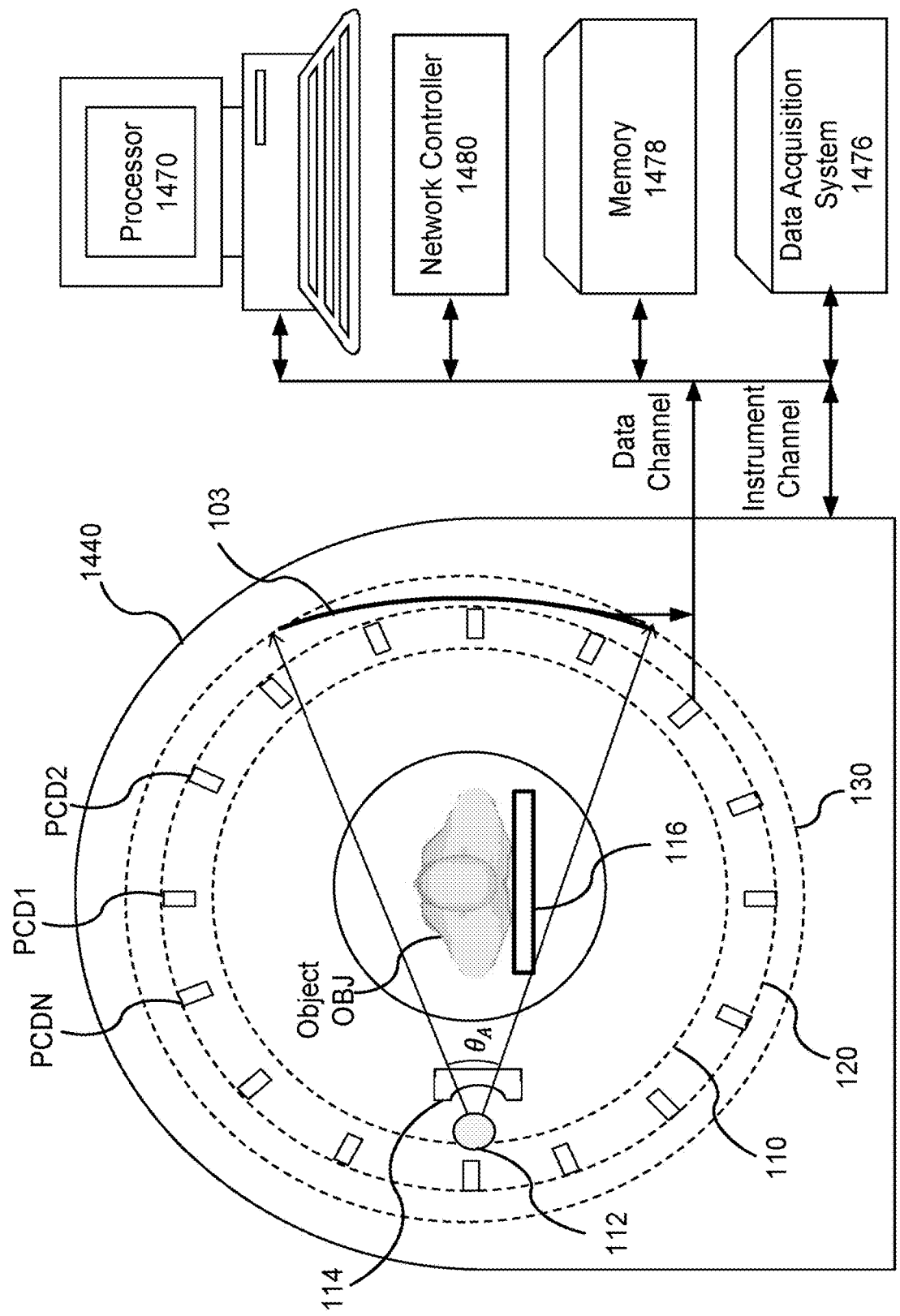
FIG. 9 shows a schematic of an implementation of a CT scanner using an energy-integrating detector array in a third-generation geometry and photon-counting detectors in a fourth-generation geometry, according to one implementation.

FIG. 9 shows another implementation of a computed tomography (CT) scanner having both energy-integrating detectors arranged in a third-generation geometry and PCDs arranged in a fourth-generation geometry. Illustrated in FIG. 9 is an implementation for placing the PCDs in a predetermined fourth-generation geometry in combination with a detector unit 103 in a predetermined third-generation geometry in a CT scanner system. The diagram illustrates relative positions among the X-ray source 112, the collimator/filter 114, the X-ray detector 103, and the photon-counting detectors PCD1 through PCDN.

In addition to the configuration of the X-ray source 112 and the detectors including the detector unit 103 and the PCDS show in FIG. 12, other types and combinations of X-ray detectors and X-ray source can be used to obtain the projection data. For example, either the detector unit 103 or the PCDS could be omitted from the scanner shown in FIG. 9 and the scanner could still obtain projection data, albeit different from the projection data obtained using the complete system shown in FIG. 12. Further, kV switching could be used with energy-integrating detectors or PCDs. In certain implementations, the PCDS can be direct X-ray detectors using semiconductors to convert the X-rays directly to photoelectrons without first generating scintillation photons. Additionally, in certain implementations, a broadband X-ray source can be used with spectrally-resolving X-ray detectors. These spectrally-resolving X-ray detectors can include PCDs in any configurations (e.g., a predetermined third-generation geometry or a predetermined fourth-generation geometry) or energy-integrating detectors preceded by respective spectral filters. In certain implementations, the X-ray source can include multiple narrow-band X-ray sources, such as in a dual source CT scanner. In general, any known combination of detector type and configuration together with any known type or combination of X-ray sources can be used to generate the projection data.

Returning to FIG. 12, FIG. 12 also shows circuitry and hardware for acquiring, storing, processing, and distributing X-ray projection data. The circuitry and hardware include: a processor 1470, a network controller 1480, a memory 1478, and a data acquisition system 1476.

In one alternative implementation, the CT scanner includes PCDs but does not include the energy-integrating detector unit 103.

As the X-ray source 112 and the detector unit 103 are housed in a gantry 1440 and rotate around circular paths 110 and 130 respectively, the photon-counting detectors PCDs and the detector unit 103 respectively detects the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 103 continuously detect the X-ray radiation that has been transmitted and output the detected signals as the detector unit 103 rotates. In one implementation, the detector unit 103 has densely placed energy-integrating detectors in predetermined channel and segment directions on the detector unit surface.

In one implementation, the X-ray source 112, the PCDs and the detector unit 103 collectively form three predetermined circular paths that differ in radius. At least one X-ray source 112 rotates along a first circular path 110 while the photon-counting detectors are sparsely placed along a second circular path 120. Further, the detector unit 103 travels along a third circular path 130. The first circular path 110, second circular path 120, and third circular path 130 can be determined by annular rings that are rotatably mounted to the gantry 1440.

Additionally, alternative embodiments can be used for placing the photon-counting detectors in a predetermined fourth-generation geometry in combination with the detector unit in a predetermined third-generation geometry in the CT scanner.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs).

The CT scanner also includes a data channel that routes projection measurement results from the photon-counting detectors and the detector unit 103 to a data acquisition system 1476, a processor 1470, memory 1478, network controller 1480. The data acquisition system 1476 controls the acquisition, digitization, and routing of projection data from the detectors. The data acquisition system 1476 also includes radiography control circuitry to control the rotation of the annular rotating frames 110 and 130. In one implementation data acquisition system 1476 will also control the movement of the bed 116, the operation of the X-ray source 112, and the operation of the X-ray detectors 103. The data acquisition system 1476 can be a centralized system or alternatively it can be a distributed system. In an implementation, the data acquisition system 1476 is integrated with the processor 1470. The processor 1470 performs functions including reconstructing images from the projection data, pre-reconstruction processing of the projection data, and post-reconstruction processing of the image data. The processor 1470 also performs the functions and methods described herein.

The pre-reconstruction processing of the projection data can include correcting for detector calibrations, detector nonlinearities, polar effects, noise balancing, and material decomposition. Additionally, the pre-reconstruction processing can include various steps of methods 300, 400, and 500.

Post-reconstruction processing can include filtering and smoothing the image, volume rendering processing, and image difference processing as needed. Additionally, the Post-reconstruction processing can include various steps of methods 300, 400, and 500.

The image-reconstruction process can be performed using filtered back-projection, iterative-image-reconstruction methods, or stochastic-image-reconstruction methods. Additionally, the image-reconstruction processing can include a combined process of reconstructing and denoising the reconstructed images using method 800.

Both the processor 1470 and the data acquisition system 1476 can make use of the memory 1476 to store, e.g., projection data, reconstructed images, calibration data and parameters, and computer programs.

The processor 1470 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 1478 can be a hard disk drive, CD-ROM drive, DVD drive, FLASH drive, RAM, ROM or any other electronic storage known in the art.

The network controller 1480, such as an Intel Ethernet PRO network interface card from Intel Corporation of America, can interface between the various parts of the CT scanner. Additionally, the network controller 1480 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
   circuitry configured to
   obtain projection data having a plurality of energy components and representing an intensity of radiation detected at a plurality of detector elements,
   generate beam-hardening-free basis-specific projection data by decomposing the obtained projection data using a first set of basis functions,
   reconstruct respective beam-hardening-free basis-specific images using the corresponding beam-hardening-free basis-specific projection data using a second set of basis functions, and
   generate respective material-component images by decomposing the beam-hardening-free basis-specific images into corresponding material components.

2. The apparatus according to claim 1, wherein the circuitry is further configured to generate the beam-hardening-free basis-specific projection data by
   performing scatter correction on the obtained projection data to separate a principal beam from a scatter beam, and
   performing a basis-specific decomposition on the principal beam as part of a process to generate the beam-hardening-free basis-specific projection data.

3. The apparatus according to claim 1, wherein the circuitry is further configured to generate the beam-hardening-free basis-specific projection data by decomposing the obtained projection data using the first set of basis functions, which are material-component basis functions, wherein the obtained projection data is decomposed into material components using a material decomposition method, and the material decomposition method includes a beam-hardening correction.

4. The apparatus according to claim 1, wherein the circuitry is further configured to generate the beam-hardening-free basis-specific projection data by
   determining respective attenuation coefficients corresponding to a plurality of radiation energies and corresponding to basis components of the first set of basis functions, and
   generating the beam-hardening-free basis-specific projection data, which include projection images corresponding to the plurality of radiation energies, wherein the projection images are determined by multiplying the respective attenuation coefficients by projection lengths corresponding to the basis components.

5. The apparatus according to claim 1, wherein the circuitry is further configured to generate the respective material-component projection data by
   calibrating a detector response of the plurality of detector elements,
   calibrating a radiation spectrum of a radiation source generating the radiation, and
   performing a basis-specific decomposition using the calibrated detector response and the calibrated radiation spectrum to correct and decompose the projection data into basis components.

6. The apparatus according to claim 1, wherein the circuitry is further configured to generate the respective material-component images by
   calibrating an image-domain material-decomposition method using first object comprising materials with known attenuation coefficients, and
   performing the image-domain material-decomposition method in accordance with prior information regarding a second object, which was traversed by the radiation when generating the projection data, to generate the material-component images from the beam-hardening-free basis-specific images.

7. The apparatus according to claim 6, wherein the circuitry is further configured to perform the image-domain material-decomposition method, which includes minimizing a regularization term according to the prior information regarding the second object.

8. The apparatus according to claim 1, wherein the circuitry is further configured to
   perform scatter correction, using the material-component images and scattering coefficients of the material components, on the obtained projection data to separate a principal beam from a scatter beam,
   perform a basis-specific decomposition on the principal beam to generate basis-specific projection data,
   generate other beam-hardening-free basis-specific projection data using the first set of basis functions and the basis-specific projection data,
   reconstruct other beam-hardening-free basis-specific images by performing computed-tomography image reconstruction on the other beam-hardening-free basis-specific projection data, and
   generate other material-component images by decomposing the other beam-hardening-free basis-specific images into the corresponding material components.

9. The apparatus according to claim 1, wherein the circuitry is further configured to
   generate the beam-hardening-free basis-specific projection data by decomposing the obtained projection data using the first set of basis functions, wherein the beam-hardening-free basis-specific projection data is monoenergetic projection data, each projection image of the monoenergetic projection data representing discrete energies of the radiation, and the first set of basis functions corresponds to material components, and
   reconstruct the respective beam-hardening-free basis-specific images from the corresponding beam-hardening-free basis-specific projection data using the second set of basis function, wherein the respective beam-hardening-free basis-specific images are monoenergetic images, each monoenergetic image representing the discrete energies of the radiation, and the second set of basis functions corresponds to the material components.

10. The apparatus according to claim 8, wherein the circuitry is further configured to iteratively repeat a loop including
performing the scatter correction, using a previous iteration of the other material-component images, on the obtained projection data to separate a current iteration of the principal beam from a current iteration of the scatter beam,
performing the basis-specific decomposition on the current iteration of the principal beam to generate a current iteration of the basis-specific projection data,
generating a current iteration of the other beam-hardening-free basis-specific projection data using the first set of basis functions and the current iteration of the basis-specific projection data,
reconstructing a current iteration of the other beam-hardening-free basis-specific images by performing computed-tomography image reconstruction on the current iteration of the other beam-hardening-free basis-specific projection data, and
generating a current iteration of the other material-component images by decomposing the current iteration of the other beam-hardening-free basis-specific images into the corresponding material components, wherein
the loop is iteratively repeated until stopping criteria are satisfied, the stopping criteria including a convergence condition, which is satisfied when a predefined norm of a difference between successive iterations of the material-component images is less than a predefined threshold.

11. The apparatus according to claim 10, wherein the circuitry is further configured to iteratively repeat the loop until the stopping criteria are satisfied, wherein the stopping criteria include a maximum-iterations condition, which is satisfied when a number of iterations of the loop is equal to or greater than a predefined iterations threshold, and the stopping criteria are satisfied when either the convergence condition or the maximum-iterations condition is satisfied.

12. An apparatus, comprising:
an X-ray source configured to transmit X-rays;
a plurality of detector elements, wherein the plurality of detector elements is configured to
detect a plurality of energy components of the X-rays, which are transmitted from the X-ray source and traverse an object before arriving and being detected at the plurality of detector elements, and
generate projection data representing an intensity of the X-rays detected at the plurality of detector elements; and
circuitry configured to
generate beam-hardening-free basis-specific projection data by decomposing the obtained projection data using a first set of basis functions,
reconstruct respective beam-hardening-free basis-specific images using the corresponding beam-hardening-free basis-specific projection data using a second set of basis functions, and
generate respective material-component images by decomposing the beam-hardening-free basis-specific images into corresponding material components.

13. The apparatus according to claim 12, wherein the circuitry is further configured to
perform scatter correction, using the material-component images and scattering coefficients of the material components, on the obtained projection data to separate a principal beam from a scatter beam,
perform a basis-specific decomposition on the principal beam to generate basis-specific projection data,
generate other beam-hardening-free basis-specific projection data using the first set of basis functions and the basis-specific projection data,
reconstruct other beam-hardening-free basis-specific images by performing computed-tomography image reconstruction on the other beam-hardening-free basis-specific projection data, and
generate other material-component images by decomposing the other beam-hardening-free basis-specific images into the corresponding material components.

14. The apparatus according to claim 12, wherein the circuitry is further configured to generate the beam-hardening-free basis-specific projection data by
determining respective attenuation coefficients corresponding to a plurality of radiation energies and corresponding to basis components of the first set of basis functions, and
generating the beam-hardening-free basis-specific projection data, which include projection images corresponding to the plurality of radiation energies, wherein the projection images are determined by multiplying the respective attenuation coefficients by projection lengths corresponding to the basis components.

15. A method, comprising:
obtaining projection data having a plurality of energy components and representing an intensity of radiation detected at a plurality of detector elements;
generating beam-hardening-free basis-specific projection data by decomposing the obtained projection data using a first set of basis functions,
reconstructing respective beam-hardening-free basis-specific images using the corresponding beam-hardening-free basis-specific projection data using a second set of basis functions, and
generating respective material-component images by decomposing the beam-hardening-free basis-specific images into corresponding material components.

16. The method according to claim 15, wherein
the generating of the beam-hardening-free basis-specific projection data by decomposing the obtained projection data using the first set of basis functions, wherein the beam-hardening-free basis-specific projection data is monoenergetic projection data, each projection image of the monoenergetic projection data representing discrete energies of the radiation, and the first set of basis functions corresponds to material components, and
the reconstructing of the respective beam-hardening-free basis-specific images includes that the beam-hardening-free basis-specific images using the second set of basis function, wherein the respective beam-hardening-free basis-specific images are monoenergetic images, each monoenergetic image representing the discrete energies of the radiation, and the second set of basis functions corresponds to material components.

17. The method according to claim 15, wherein the generating of the respective material-component projection data includes
calibrating a detector response of the plurality of detector elements,
calibrating a radiation spectrum of a radiation source generating the radiation, and
performing a basis-specific decomposition using the calibrated detector response and the calibrated radiation spectrum to correct and decompose the projection data into basis components.

18. The method according to claim 15, wherein the generating of the respective material-component images includes
  calibrating an image-domain material-decomposition method using a first object comprising materials with known attenuation coefficients, and
  performing the image-domain material-decomposition method in accordance with prior information regarding a second object, which was traversed by the radiation when generating the projection data, to generate the material-component images from the beam-hardening-free basis-specific images.

19. The method according to claim 15, further comprising:
  performing scatter correction, using the material-component images and scattering coefficients of the material components, on the obtained projection data to separate a principal beam from a scatter beam,
  performing a basis-specific decomposition on the principal beam to generate basis-specific projection data,
  generating other beam-hardening-free basis-specific projection data using the first set of basis functions and the basis-specific projection data,
  reconstructing other beam-hardening-free basis-specific images by performing computed-tomography image reconstruction on the other beam-hardening-free basis-specific projection data, and
  generating other material-component images by decomposing the other beam-hardening-free basis-specific images into the corresponding material components.

20. A non-transitory computer readable storage medium including executable instruction, wherein the instructions, when executed by circuitry, cause the circuitry to perform the method according to claim 15.

* * * * *